United States Patent [19]

Ondetti

[11] 4,108,886
[45] Aug. 22, 1978

[54] THIOPROPANOYLAMINO ACID DERIVATIVES

[75] Inventor: Miguel Angel Ondetti, Princeton, N.J.

[73] Assignee: E. R. Squibb & Sons, Inc., Princeton, N.J.

[21] Appl. No.: 776,792

[22] Filed: Mar. 11, 1977

[51] Int. Cl.² .................. C07C 153/09; C07D 207/04; C07C 61/06; C07C 101/04
[52] U.S. Cl. ........................ 260/455 R; 260/326.2; 260/514 J; 260/534 S; 424/274; 424/301; 424/319
[58] Field of Search .............. 260/455 R, 514 J, 534 S

[56] References Cited

U.S. PATENT DOCUMENTS

| 3,098,078 | 7/1963 | Druey et al. ..................... 260/455 R |
| 3,897,480 | 7/1975 | Mita et al. ........................ 260/455 R |

*Primary Examiner*—Lewis Gotts
*Assistant Examiner*—Robert C. Whittenbaugh
*Attorney, Agent, or Firm*—Lawrence S. Levinson; Merle J. Smith

[57] ABSTRACT

New thiopropanoylamino acid derivatives which have the formula

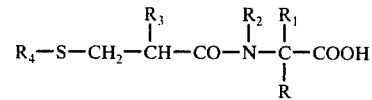

wherein
R and $R_1$ each is lower alkyl;
$R_2$ and $R_3$ each is hydrogen or lower alkyl; or $R_1$ can be joined to either R or to $R_2$ in a five membered ring;
$R_4$ is hydrogen, lower alkanoyl or benzoyl;
are useful as hypotensive agents.

7 Claims, No Drawings

THIOPROPANOYLAMINO ACID DERIVATIVES

DETAILED DESCRIPTION OF THE INVENTION

This invention relates to new thiopropanoylamino acid derivatives which have the formula

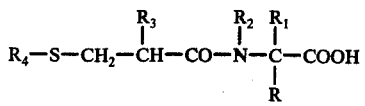

In formula I and throughout this specification the symbols have the meanings described below.

R and $R_1$ each is lower alkyl.

$R_2$ and $R_3$ each is hydrogen or lower alkyl.

In addition $R_1$ can be joined to either R or $R_2$ in a polymethylene chain to complete a five membered ring containing only carbon and hydrogen atoms or one nitrogen and the remainder carbon and hydrogen. That is, $R_1$ and R together can form a tetramethylene chain which completes a cyclopentane ring with the carbon to which they are attached. Alternatively, $R_1$ can join with $R_2$ in a trimethylene chain to complete a pyrrolidine ring with the nitrogen and carbon atoms to which they are attached.

$R_4$ is hydrogen, lower alkanoyl or benzoyl.

The lower alkyl groups are straight or branched chain hydrocarbon radicals having up to seven carbon atoms, e.g., methyl, ethyl, propyl, isopropyl, butyl, sec.butyl and the like. The $C_1-C_4$ and especially $C_1-C_2$ alkyl groups are preferred.

The lower alkanoyl groups are the acyl radicals of the lower ($C_2-C_7$) fatty acids, e.g., acetyl, propionyl, butyryl, isobutyryl and the like. The members mentioned, and especially acetyl, are preferred.

Preferred members of the invention are those compounds of formula I wherein $R_1$ is joined to R or $R_2$ in a five membered ring. Especially preferred are those compounds wherein R and $R_1$ join to form a cyclopentane ring.

The compounds of formula I are produced from amino acid compounds having the formula

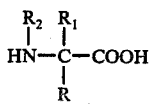

by reacting such an acid with a halopropanoyl halide having the formula

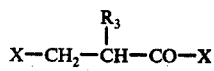

wherein each X is halogen, preferably chlorine or bromine, to obtain an intermediate having the formula

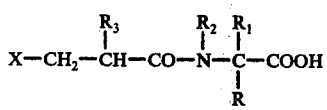

Treatment of this intermediate with a mercaptan

yields a product having the formula

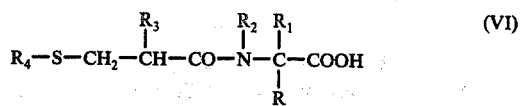

$R_4$ in this instance is other than hydrogen, i.e., the acyl groups lower alkanoyl or benzoyl. By treating the acyl derivative of formula IV with ammonia or concentrated ammonium hydroxide, a compound of formula VI wherein $R_4$ is hydrogen is derived.

Additional experimental details can be found in the illustrative examples below.

The compounds of this invention are angiotensin converting enzyme inhibitors and are useful as hypotensive agents, particularly for the reduction of angiotensin dependent hypertension. By administering a composition containing one or a combination of angiotensin converting enzyme inhibitor of this invention to a hypertensive mammal, it intervenes in the renin → angiotensin I → angiotensin II sequence and the hypertension is reduced or alleviated.

A single dose, or preferably two to four divided daily doses, provided on a basis of about 1 to 1000 mg. per kilogram per day and especially about 10 to 200 mg. per kilogram per day is appropriate to bring about a reduction in elevated blood pressure. The animal model experiments described by Engel et al., Proc. Soc. Exp. Biol. Med. 143, 483 (1973) provide a valuable guide.

The composition is preferably administered orally, but it can also be administered subcutaneously, intramuscularly, intravenously or intraperitoneally. The compound or compounds of formula I can be formulated as tablets, capsules or elixirs for oral administration. Sterile solutions or suspensions can be used for parenteral use.

About 50 to 1500 mg. of a compound or compounds of formula I can be compounded with a physiologically acceptable vehicle, carrier, excipient, binder, preservative, stabilizer, flavor, etc., in a conventional unit dosage form as called for by accepted pharmaceutical practice. The amount of active substance is selected so as to provide a dosage in the range indicated.

The following examples are illustrative of the invention and represent preferred embodiments. All temperatures are in degrees Celsius.

EXAMPLE 1

2-[(3-Benzoylthiopropanoyl)amino]-2-methylpropanoic acid

α-Aminoisobutyric acid (5.15 g.) is dissolved in 59 ml. of 0.85 N sodium hydroxide while stirring in an ice bath. To this, 25 ml. of 2 N sodium hydroxide is added, followed to 8.5 g. of 3-bromopropionyl chloride. The bath is removed, and the pH adjusted to 7.3 with 2N sodium hydroxide. After 2 hours, a solution of 7.5 g. of thiobenzoic acid and 4.8 g. of potassium carbonate in 50 ml. of water is added. The reaction mixture is stirred overnight at room temperature, acidified with concentrated hydrochloric acid and extracted with ethyl acetate. The organic layer is dried and concentrated to dryness, yield 13.1 g. The product, 2-[(3-benzoylthiopropanoyl- )amino]-2-methylpropanoic acid, is crystallized from ethylacetate-ether, yield 5.4 g., m.p. 142°–143°.

EXAMPLE 2

2-[(3-Mercaptopropanoyl)amino]-2-methylpropanoic acid 2.8 g. of the product of Example 1 is treated with a mixture of 20 ml. water and 20 ml. of concentrated ammonium hydroxide solution under an argon blanket for one hour. The benzmide precipitate is filtered and the filtrate is extracted twice with ethyl acetate. The aqueous phase is concentrated in vacuo, acidified with concentrated hydrochloric acid and extracted with ethyl acetate. The organic layer is dried and concentrated to dryness in vacuo and the residual product 2-[(3-mercaptopropanoyl)amino]-2-methylpropanoic acid, is crystallized from acetonitrile, yield 1.2 g., m.p. 169°–170°.

EXAMPLE 3

1-[(3-Acetylthiopropanoyl)amino]cyclopentane carboxylic acid

1-Aminocyclopentane-1-carboxylic acid (6.45 g.) is dissolved in 50 ml. of 1N sodium hydroxide solution and stirred in an ice bath. To this 25 ml. of 2N sodium hydroxide solution is added, followed immediately with 8.5 g. of 3-bromopropionyl chloride. The bath is removed and the pH is about 7. Some crystals come out of solution. After 3.5 hours at room temperature, 54 ml. of 1N sodium hydroxide solution is added and everything goes into solution. This is followed immediately with 4.12 g. of thiolacetic acid. An additional 5 ml. of 1 N sodium hydroxide is added to bring the pH to near 8. After standing overnight, the mixture is acidified with concentrated hydrochloric acid, extracted with ethyl acetate, dried over magnesium sulfate, and concentrated to dryness in vacuo. The product, 1-[(3-acetylthiopropanoyl)amino]cyclopentane carboxylic acid, is first crystallized from ethyl acetate and hexane. This material is recrystallized from ethyl acetate, yield 3.655g., m.p. 127°–128°.

EXAMPLE 4

1-[(3-Mercaptopropanoyl)amino]cyclopentane carboxylic acid

The product of Example 3 (1.04 g.) is treated for 1 hour, under an argon blanket, with a solution of 2.4 ml. of water and 1.6 ml. of concentrated ammonium hydroxide solution. The reaction mixture is diluted with water, extracted twice with ethyl acetate, the aqueous phase is acidified with concentrated hydrochloric acid and extracted into ethyl acetate. The ethyl acetate extract is dried over magnesium sulfate and concentrated in vacuo. The product, 1-[(3-mercaptopropanoyl)amino]cyclopentane carboxylic acid, is crystallized from ethyl acetate and recrystallized from acetonitrile, yield 343 mg., m.p. 175°–176°.

EXAMPLE 5

1-(3-Mercaptopropanoyl)-2-methylproline

By substituting 2-methylproline for the α-aminoisobutyric acid in the procedure of Example 1, and then submitting the product to the procedure of Example 2, 1-(3-benzoylthiopropanoyl)-2-methylproline and 1-(3-mercaptopropanoyl)-2-methylproline are obtained.

EXAMPLE 6

1-(3-Mercapto-2-methylpropanoylamino)cyclopentane carboxylic acid

By substituting 3-bromo-2-methylpropionyl chloride for the 3-bromopropionyl chloride in the procedure of Example 3, and then submitting the product to the procedure of Example 4, 1-(3-acetylthio-2-methylpropanoylamino)cyclopentane carboxylic acid and 1-(3-mercapto-2-methylpropanoylamino)cyclopentane carboxylic acid are obtained.

EXAMPLE 7

1-(3-Mercapto-2-methylpropanoyl)-2-methylproline

By substituting 2-methylproline for the 1-aminocyclopentane-1-carboxylic acid and 3-bromo-2-methylpropionyl chloride for the 3-bromopropionyl chloride in the procedure of Example 3, and then submitting the product to the procedure of Example 4, 1-(3-acetylthio-2-methylpropanoyl)-2-methylproline and 1-(3-mercapto-2-methylpropanoyl)-2-methylproline are obtained.

What is claimed is:

1. A compound of the formula

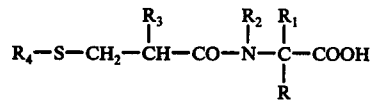

wherein R and $R_1$ each is lower alkyl, $R_2$ and $R_3$ each is hydrogen or lower alkyl;

or $R_1$ joins with R to complete a cyclopentane ring; and $R_4$ is hydrogen, lower alkanoyl or benzoyl.

2. A compound as in claim 1 wherein $R_1$ and R join to complete a cyclopentane ring.

3. A compound as in claim 1 wherein $R_2$, $R_3$ and $R_4$ each is hydrogen.

4. A compound as in claim 1 wherein R and $R_1$ each is methyl; and $R_2$, $R_3$ and $R_4$ each is hydrogen.

5. A compound as in claim 1 wherein R and $R_1$ join to complete a cyclopentane ring; $R_2$ and $R_3$ each is hydrogen; and $R_4$ is acetyl.

6. A compound as in claim 1 wherein R and $R_1$ join to complete a cyclopentane ring; and $R_2$, $R_3$ and $R_4$ each is hydrogen.

7. A compound as in claim 1 wherein R and $R_1$ join to complete a cyclopentane ring; $R_2$ and $R_4$ each is hydrogen, and $R_3$ is methyl.

* * * * *